(12) United States Patent
Pagani

(10) Patent No.: US 8,927,477 B2
(45) Date of Patent: Jan. 6, 2015

(54) SANITARY AGENT COVERED BY A FILM

(75) Inventor: Fabio Pagani, Malcesine sul Garda (IT)

(73) Assignee: RE.LE.VI. S.p.A., Rodigo (Mantova) (IT)

( * ) Notice: Subject to any disclaimer, the term of this patent is extended or adjusted under 35 U.S.C. 154(b) by 19 days.

(21) Appl. No.: 13/814,416

(22) PCT Filed: May 27, 2011

(86) PCT No.: PCT/IB2011/001160
§ 371 (c)(1),
(2), (4) Date: Feb. 5, 2013

(87) PCT Pub. No.: WO2012/017276
PCT Pub. Date: Feb. 9, 2012

(65) Prior Publication Data
US 2013/0171227 A1    Jul. 4, 2013

(30) Foreign Application Priority Data

Aug. 6, 2010    (IT) .............................. RE2010A0066

(51) Int. Cl.
| | | |
|---|---|---|
| *C11D 17/04* | (2006.01) | |
| *C11D 17/00* | (2006.01) | |
| *A01N 25/34* | (2006.01) | |
| *E03D 9/02* | (2006.01) | |

(52) U.S. Cl.
CPC .......... *C11D 17/044* (2013.01); *C11D 17/0056* (2013.01); *C11D 17/042* (2013.01); *A01N 25/34* (2013.01); *E03D 9/022* (2013.01)
USPC ............... 510/192; 510/193; 510/447; 4/224; 4/227.1; 134/34; 422/5; 422/28; 428/343

(58) Field of Classification Search
USPC ..................... 252/181, 186.35; 424/401, 408; 510/191, 192, 193, 363, 441, 447, 473; 4/223, 227.1
See application file for complete search history.

(56) References Cited

U.S. PATENT DOCUMENTS

| | | | |
|---|---|---|---|
| 4,460,490 | A | 7/1984 | Barford et al. |
| 6,667,286 | B1 | 12/2003 | Dettinger et al. |

FOREIGN PATENT DOCUMENTS

| | | | | | |
|---|---|---|---|---|---|
| EP | 1086199 | A1 | | 3/2001 | |
| EP | 2141221 | A1 | | 1/2010 | |
| EP | 2141221 | A1 | * | 1/2010 | ............. C11D 17/04 |
| EP | 2196531 | A1 | * | 6/2010 | ............. C11D 17/00 |
| EP | 2196531 | A1 | | 6/2010 | |
| WO | 2008100393 | A1 | | 8/2008 | |

* cited by examiner

*Primary Examiner* — Jane C Oswecki
(74) *Attorney, Agent, or Firm* — Volpe and Koenig, P.C.

(57) ABSTRACT

A sanitary agent for treatment of a sanitary appliance includes a solid or semi-solid active body, designed to adhere to a wall of the sanitary appliance and including a treatment compound having at least an active element for treatment of the sanitary appliance. The body has an external surface thereof covered by a water-soluble film. In this way, the sanitary agent can be manipulated by hand for application thereof to a moist ceramic wall of a sanitary appliance to be treated, without the user's hands entering into contact with the components of the sanitary agent itself. Furthermore, any undesired loss of the components of the sanitary agent is avoided; these can be due to deformation of the sanitary agents before use thereof, displacements thereof and/or any dripping. A method for applying the sanitary agent for deterging, disinfecting and/or perfuming the sanitary appliance is also provided.

8 Claims, No Drawings

SANITARY AGENT COVERED BY A FILM

TECHNICAL FIELD

The present invention relates to a sanitary agent for cleaning, disinfecting and/or perfuming a sanitary appliance and to a method for applying the sanitary agent to the sanitary appliance.

BACKGROUND ART

Sanitary appliances, for example hygienic toilet bowls or urinals fixed to a wall, have to be subjected to repeated cleaning and disinfecting operations in order to be able to maintain adequate hygienic sanitary conditions.

The prior art comprises hanging sanitary agents by means of hooking devices positioned in the water closet container, where one exists; the emission of the sanitary agent occurs at each discharge flush operation into the bowl.

Also known are sanitary agents which are fixed to the perimeter edge of the toilet bowl by means of a support; these sanitary agents are normally inserted in particular devices, like cages, provided with the support means, such as for example a plastic bracket, and which also include slits and/or holes such as to enable a portion of the sanitary agent to exit at each flush of the water.

The above-described sanitary agents, when struck by the water which irrigates the toilet bowl, enrich the water with the substances contained in the agents, thus providing the elements required for deterging, descaling, deodorising and/or disinfecting the bowl.

However, the above-described hygienic devices present some drawbacks, such as for example not guaranteeing an adequate anchoring to the perimeter edge of the bowl due to the fragility of the support means, with the consequence that there might be a possible accidental fall of the sanitary agent contained in the device into the toilet bowl.

Further, these devices are not very practical and hygienic; during manual cleaning of the edge of the toilet bowl or during the cleaning of the inside of the bowl by use of the toilet brush, the support means fixed to the edge of the bowl can be accidentally shifted and it is therefore necessary to reposition it. Further, on substitution of the sanitary agent, due to its consumption, it is necessary to act manually with ensuing operative and hygienic difficulties for the user, as the devices are often positioned in poorly-accessible places, in any case not ideal from the hygienic point of view.

Further, it is difficult to apply these devices to urinals, as urinals are generally lacking in edges or parts in relief on which the support means can be fixed. In the case of urinals or urinal bowls, pastilles are often used, positioned in the lower part thereof, at the position of the drain. However, these pastilles are generally partly washed away by the water flush and also cause undesired backsplash.

In recent times alternative solutions have been looked for, by eliminating the presence of the devices having a support means to be fixed to the perimeter edge of the bowl.

The prior art comprises certain solutions to the above-cited problem, in which sanitary agents, in particular solid or semi-solid soaps, can adhere stably to the internal wall of a WC bowl or a urinal in order to be subjected to regular water flushes.

For example, the international application published at no. WO2008/100393 in the name of Johnson and Sons proposes a solid soap able to adhere to the surface of the bowl and guarantee at the same time adequate cleaning thereof; however, this soap has to contain a very high amount of solid surfactant substance, between 75% and 99% in weight of the weight of the soap. European patent EP 1 086 199 in the name of Buck-Chemie GmbH describes a sanitary agent which can be applied directly on the surface of the sanitary appliance, the sanitary agent having a viscosity of at least 15,000 mPas and comprising an adhesion promoter such as poly oxy alcohol alkane, cellulose, etc. Further, EP application 2 141 221 in the name of Manitoba described a detergent pastille having a substantially flat adhesive surface for anchoring to a wall of the WC bowl and a shell-shaped surface such as to be subjected to the action of the flush water.

A problem of the above-described sanitary agents described in the above patent applications is that the user is usually required to manipulate the sanitary agents during their stage of application to the sanitary appliances to be treated. The manipulation is normally done in two ways: through the use of an applicator used for transferring the detergent agent, arranged thereon, onto the wall of the toilet bowl by means of compression there-against, or by manual application, thus by gripping the detergent agent with the hand and resting in on the wall, exerting a pressure thereon which is sufficient to cause its adhesion to the wall.

In order to prevent the detergent agent from coming into contact with the skin of the hand, a solution adopted in the art is to wrap the sanitary agent in a traditional protective film, which is partially removed on the side to be attached to the sanitary appliance immediately after use. Thereafter, the sanitary agent is attached to the wall of the sanitary appliance, after which the remaining part of the protective film is removed.

However, this operation is not comfortable and has the risk of a part of the protective film falling into the toilet bowl, or even the product itself doing so; further, the hand may still come into contact with the sanitary agent.

Further, another problem consists in the fact that often, before use, the known sanitary agents deform, with the consequence that the adhesive layers of the sanitary agents themselves displace, slipping downwards, or attach in an undesired way to the hands or other objects which they come into contact with.

Today there is still a particular demand for a solution to the technical problem of having a sanitary agent which enables a user to avoid direct contact with the components of the agent itself during application thereof and thus prevents undesired loss of the components of the sanitary agent before and during use thereof.

Therefore the aim of the present invention is to provide a sanitary agent for treatment of a sanitary appliance and a method of application of the sanitary agent to the sanitary appliance, which constitute a solution to the above-mentioned technical problems of the cited prior art.

DISCLOSURE OF INVENTION

In a first aspect, the present invention relates to a sanitary agent to be used for deterging, disinfecting and/or perfuming a sanitary appliance, the sanitary agent comprising an active body, solid or semi-solid, having adhesive agents which make the body capable to adhere stably to the wall of a sanitary appliance in order to be subjected to several regular water flushes and including a treatment compound having at least an active element for treatment of the sanitary appliance.

The present Applicant has found that said sanitary agent for treating a sanitary appliance, characterised in that the body has an external surface covered with a water-soluble film, is capable of enabling manipulation of the sanitary agent by hand for application thereof to a moist ceramic wall of a sanitary appliance to be treated, without entering into contact with components thereof and preventing any undesired loss of the components of the sanitary agent due to deformations of the sanitary agents before use thereof, displacements thereof and/or any dripping away.

Further, in this way the advantage is gained of adequately conserving the product internally of the sales packaging and of being able to use any traditionally-known body as an active body.

In this context and in the following claims, the term "sanitary appliance" is understood to mean a water-closet toilet bowl, a urinal bowl, a urinal or any other like apparatus which is usually subjected to water flushes in order to maintain cleanliness and hygiene thereof.

In this context, and in the following claims, the term "treatment of a sanitary appliance" is understood to mean cleaning, hygienising, disinfecting, perfuming and removing limescale, and other like operations applicable to the sanitary appliance.

In this context and in the following claims, the term "active element for the treatment" is understood to mean an element dedicated to cleaning, deterging, foaming, perfuming, deodorising, disinfecting, water-colouring, polishing, or any other element which is soluble in water and useful for the treatment to which the sanitary appliance is to be subjected.

In this context and in the following claims, the term "semi-solid body" is intended to mean a body having a pasty consistency, or having a consistency which is such as to be slightly modified in shape by manual pressure, but such as to maintain over time the given shape, even following the action of weak external forces, such as a water flush or discharge.

The external surface of the sanitary agent is preferably substantially completely covered by the water-soluble film; more preferably the covering is extended tightly about the external surface of the active body of the sanitary agent such as to obtain a layer of homogeneous contact which is free of evident roughness.

The water-soluble film in contact with a moist surface is preferably able to realise an adhesion thereto.

Further, the water-soluble film is preferably selected from a group consisting of poly vinyl acetate, PVOH, or biodegradable plastic, such as for example the plastic obtained from corn starch and available on the market under the name Mater-Bi®, manufactured by Novamont. The water-soluble film is more preferably made of poly vinyl acetate or poly vinyl alcohol.

In this way an advantage is attained, that is, when the sanitary agent of the present invention covered with the water-soluble film is placed in contact with a slightly-moist surface of the sanitary appliance to be treated, adhesion of the active body of the sanitary agent to the moist surface is facilitated, before the water-soluble film completely solubilises.

The water-soluble film preferably has a thickness of from 5 to 500 micron, and more preferably from 10 to 100 micron, and still more preferably from 20 to 50 micron.

The water-soluble film preferably has a density of from 0.25 to 5 g/cm$^3$, more preferably from 1 to 3 g/cm$^3$.

In this way, the water-soluble film enables packaging of small objects, i.e. with a length of the order of from a few millimeters to a few tens of centimeters.

As already said hereinabove, the sanitary agent active body, has adhesive agents making it capable to adhere stably to the internal wall of a WC bowl or a urinal in order to stand up when subjected to several regular water flushes. In a first preferred embodiment, the sanitary agent comprises an adhesive layer positioned on a portion of the external surface of the active body covered with the water-soluble film.

This adhesive layer is able to realise a reinforced adhesion to the wall of the sanitary appliance.

In a second preferred embodiment, the sanitary agent comprise an adhesive element dispersed in the material of the active body, preferably dispersed in the treatment composition of the sanitary agent. In this way, a reinforced adhesion to the wall of the sanitary appliance is obtained, realised by means of the adhesive component dispersed in the treatment composition.

Independently of the preferred embodiments described above, the adhesive element can be any adhesive able to guarantee good adhesion between the wall of the sanitary appliance and the sanitary agent itself; useful adhesive agents can be, for example, though not limited to, poly oxy alcohol alkanes, cellulose and derivatives of cellulose, etc.

The active body for the treatment of the sanitary appliance can be any traditional body known in the art, solid or semi-solid, able to adhere to the wall of the sanitary appliance.

Preferably the active body includes a treatment compound having at least an active element for treatment of the sanitary appliance, where the active element is a detergent element, a perfume or a disinfectant.

The quantity of the at least an active element is preferably comprised in the interval from 1-75% in weight with respect to the total weight of the sanitary agent.

The at least a surfactant is preferably selected from a group consisting of non-ionic surfactants, anionic surfactants, cationic surfactants, amphoteric surfactants, and combinations thereof.

The non-ionic surfactants are preferably selected from the group consisting of long-chain alcohols (from about 10 to about 20 carbon atoms), such as polyoxyethylene derivatives of fatty acids, starch alkanols of fatty acids, alkyl polyglucosides (APG), natural and/or synthetic etoxylated alcohols, amine oxides.

The anionic surfactants are preferably selected from the group consisting of compounds having carbon atom chains ending with a carboxylate or sulphanate group, such as for example soaps, alkyl benzene sulphonates (LAS/ABS), alkyl ether sulphates (LES/AES), alkyl sulphates (LS/AS), α-olefin sulphonates (AOS), alkyl ether carboxylates, sulphosuccinates, aromatic sulphonates.

The cationic surfactants are preferably selected from the group consisting of long carbon atom chains (from about 10 to about 20 carbon atoms) terminating with a quaternary amine group, such as for example alkyl hydroxyethyl dimethyl ammonium chloride, banzalconium chloride, cetyl-trimethyl ammonium bromide or chloride, hexadecyl-trimethyl ammonium bromide or chloride, and the like.

The surfactant amphoterics are preferably selected from a group consisting of amino carboxyl acids, alkyl betaine, such as for example 12 betaine, starch alkyls, propyl betaine, and amphoacetates.

More preferably, the at least a surfactant is a mixture of at least a non-ionic surfactant and/or at least an anionic surfactant.

The quantity of the at least a surfactant is comprised in the range from 25-75%, more preferably in the range from 30-70% in weight with respect to the total weight of the sanitary agent.

The treatment composition preferably comprises at least an inorganic salt; more preferably, the at least an inorganic salt is selected from among the group consisting in sulphates in various stages of hydration, monovalent and bivalent metals, such as for example sodium sulphate or magnesium sulphate; monovalent and bivalent metal carbonates and bicarbonates, such as for example sodium carbonate, magnesium carbonate and sodium bicarbonate; monovalent and bivalent metal chlorides, such as for example sodium chloride.

The quantity of the at least an inorganic salt is preferably comprised in the range from 10-70%, and more preferably in the range from 10-20% in weight with respect to the total weight of the sanitary agent.

The treatment compound can preferably further comprise various agents, such as for example bleaches, perfumes, disinfectants, colorants, dispersants, plastifiers, in quantities from 0.1 to 30% in weight with respect to the total weight of the sanitary agent.

In a second aspect, the present invention relates to a method for applying a sanitary agent such as the ones described herein above to a sanitary appliance in order to deterge, disinfect and/or perfume the sanitary appliance.

In particular, the present invention relates to a method for applying a sanitary agent to a sanitary apparatus, which sanitary agent comprises an active body, solid or semi-solid, including a treatment composition having at least an active element for treatment of the sanitary apparatus, in which the active body has an external surface covered with a water-soluble film; the method comprising stages of:

a) applying the sanitary agent to a moist wall of the sanitary appliance;
b) subjecting the water-soluble film to a series of water flushes up to complete removal of the film, such that the active body of the sanitary agent is exposed to the action of the flush water of the sanitary appliance.

In this way, at the moment of use, the presence of the water-soluble film enables the sanitary agent to grip without the user's entering into contact with the active components thereof, and to bring the sanitary agent into contact with the wall of the sanitary appliance without having to remove the protective film manually.

Following the series of water flushing operations, the water-soluble film is completely solubilised; in this way, the sanitary agent is destined to be exposed to the action of the water flushes in order to commence performing its function of deterging, disinfecting and/or perfuming the sanitary appliance, becoming solubilised in the water of the flush of the appliance itself.

Stage a) of the method of the above-described invention preferably comprise following stages:

a1) pressing the sanitary agent against the moist wall of the sanitary appliance;
a2) waiting for the partial removal by solubilisation of the water-soluble film in the contact zones between the sanitary agent and the moist wall of the sanitary appliance, and maintaining it pressed up until the adhesion of the sanitary agent to the wall has been realised.

In this way, by keeping the sanitary agent pressed against the wall of the sanitary appliance to be treated for the time required, the water-soluble film, having a (comparatively good) adhesive power, at the moment of contact with the moist surface, enables a good adhesion to be obtained between the moist wall and the sanitary agent itself.

Further characteristics and advantages of the present invention will more clearly emerge from an examination of the detailed description of non-exclusive preferred embodiments thereof, by way of non-limiting example.

BEST MODE FOR CARRYING OUT THE INVENTION

Example 1

Sanitary Agent 1 (Invention)

The first treatment compound for a sanitary appliance was prepared. The compound comprised the non-ionic surfactant marketed under the name of mergital® CS25(cethearet25) by Cognis, the non-ionic surfactant marketed under the name of comperlan® 100 by Cognis, the non-ionic surfactant marketed under the name glucopon® by Cognis, the anionic surfactant alkyl sulphate marketed under the name Texapon® V95 by Cognis, sodium sulphate and a perfume in percentages as follows:

| | |
|---|---|
| Non-ionic surfactant mergital ® CS25 (cethearet25) | 39% |
| Non-ionic surfactant comperlan ® 100 | 8% |
| Non-ionic surfactant glucopon ® 50 g | 5% |
| Anionic surfactant alkyl sulphate Texapon ® V95 | 2% |
| Sodium sulphate | 38% |
| Perfume | 5% |
| Foamer DERIPHAT ® 160 C (Cognis) | 3% |

Non-ionic surfactant mergital® CS25 (cethearet25) 39%
Non-ionic surfactant comperlan® 100 8%
Non-ionic surfactant glucopon® 50 g 5%
Anionic surfactant alkyl sulphate Texapon® V95 2%
Sodium sulphate 38%
Perfume 5%
Foamer DERIPHAT®160 C (Cogins) 3%

The first treatment compound was prepared by mixing the various components in a 1-kg laboratory vertical-arm mixer at ambient temperature, leaving it to mix for about 30 minutes up to obtaining a homogeneous, plastic and modellable paste.

The sanitary agent 1 of the first preferred embodiment of the invention presented as a semi-solid active body, with a substantially rectangular shape of 60×20 millimeters, including the first treatment compound and comprising an adhesive layer positioned on a portion of the external surface of the active body. The following was spread on the adhesive layer: 0.5 grams of a suitable adhesive agent. Thus a sanitary agent 1 was obtained having a total weight of 12 grams.

The external surface was then wrapped completely with a water-soluble film made of poly vinyl acetate, 25 micron thick and having a density of 1.25 g/cm$^3$.

At moment of use for deterging a toilet bowl, first a flush was performed such as to moisten the walls of the bowl; then the first sanitary agent, wrapped in the water-soluble film, was manually gripped and applied directly, with a slight pressure, for about ten seconds to a zone of the moistened bowl. On contact with the moist part of the bowl wall, the water-soluble film quickly solubilised (in few seconds), thus enabling the active and adhesive body of the sanitary agent to adhere to the toilet bowl. Then there was a pause of about one minute, in order to obtain good adhesion of the sanitary agent 1 to the wall. Then a series of 4-5 flushes was performed up to when the remaining portion of water-soluble film solubilised, thus enabling the active body of the sanitary agent 1 to commence its detergent action at each new flush of the toilet.

In this way, by using the sanitary agent 1 of the present invention protected by the water-soluble film, the advantage was obtained of being able to manipulate the sanitary agent for its application to the moist ceramic wall of a sanitary appliance to be treated without entering into contact with the components thereof. Further, the film also enabled protection of the sanitary agent up to the moment of its use, preventing any undesired loss of components of the sanitary agent due to deformation of the sanitary agents before use thereof, displacements thereof and/or any dripping. Further, the film does not require removal, so additional manipulations after simple pressing are avoided; thus risk of the film or the product falling into the water are avoided.

Sanitary Agent 2 (Invention)

Like sanitary agent 1, sanitary agent 2 was prepared, which was different from sanitary agent 1 in that the adhesive element was dispersed in the material of the active body, instead of being applied to the adhesive layer positioned on the external surface of the active body.

Treatment compound 2 comprised:

| | |
|---|---|
| Non-ionic surfactant mergital CS25 (cethearet25) | 39% |
| Non-ionic surfactant comperlan100 | 8% |
| Non-ionic surfactant glucopon 50 g | 5% |
| Anionic surfactant alkyl sulphate Texapon V95 | 2% |
| Sodium sulphate | 38% |
| Perfume | 5% |
| Adhesive agent | 1% |
| Foamer DERIPHAT 160 C (Cognis) | 2% |

The treatment compound 2 mixture was prepared similarly to what was set out in relation to the first example.

The sanitary agent 2, obtained using the treatment compound 2, presented as a semi-solid active body, having a substantially circular shape with a diameter of about 50 mm.

The external surface was then completely wrapped with a water-soluble film made of poly vinyl acetate being 25 micron thick and having a density of $1.25$ g/cm$^3$.

The sanitary agent 2 was subjected to the same application treatment as the toilet bowl previously described with reference to the sanitary agent 1.

In this case too, the water-soluble film solubilised first partially at the contact zone between the wall of the toilet bowl and the sanitary agent, enabling good adhesion between the two elements, subsequently freeing the active body of the sanitary agent 2, enabling it to commence the toilet bowl treatment operations on the action of the toilet flushes.

The invention claimed is:

1. A sanitary agent for treatment of a sanitary appliance, comprising:
    a solid or semi-solid active body including a treatment compound having at least an active element for treatment of the sanitary appliance, the active body comprising an external surface thereof covered by a water-soluble film, wherein the active body is adapted to adhere to a wall of the sanitary appliance by an adhesive layer, positioned on at least a portion of the external surface of the active body covered with the water-soluble film or by an adhesive element, dispersed in a material of the active body.

2. The sanitary agent of claim 1, wherein the water-soluble film, when in contact with a moist surface, is adhering thereto.

3. The sanitary agent of claim 1, wherein the water-soluble film is selected from the group consisting of: poly vinyl acetate, PVOH, a biodegradable plastic and combinations thereof.

4. The sanitary agent of claim 1, wherein the adhesive element is dispersed in the treatment compound.

5. The sanitary agent of claim 1, wherein the at least an active element is a detergent element, a perfume or a disinfectant.

6. The sanitary agent of claim 1, wherein the treatment compound comprises at least a surfactant.

7. A method for applying a sanitary agent to a sanitary appliance, the sanitary agent comprising:
    a solid or semi-solid active body which includes a treatment compound having at least an active element for treatment of the sanitary apparatus, and
    a water-soluble film covering the external surface of the active body,
    wherein the active body is able to adhere to a wall of the sanitary appliance by an adhesive layer, positioned on at least a portion of the external surface of the active body covered with the water-soluble film, or by an adhesive element, dispersed in a material of the active body,
    the method comprising steps of:
        a) applying the sanitary agent to a moist wall of the sanitary appliance;
        b) subjecting the water-soluble film to a series of water flushes up to complete removal of the film, such that the active body of the sanitary agent is exposable to the action of the flush water of the sanitary appliance.

8. The method of claim 7, wherein step a) comprises following sub steps:
    a1) pressing the sanitary agent against the moist wall of the sanitary appliance;
    a2) waiting for the partial removal by solubilisation of the water-soluble film in the contact zones between the sanitary agent and the moist wall of the sanitary appliance, and maintaining the water-soluble film pressed up until the adhesion of the sanitary agent to the wall has been realized.

\* \* \* \* \*